US00PP10167P

United States Patent [19]

Evison

[11] Patent Number: Plant 10,167

[45] Date of Patent: Dec. 30, 1997

[54] CLEMATIS PLANT NAMED 'EVITWO'

[75] Inventor: Raymond J. Evison, Guernsey, Great Britain

[73] Assignee: Poulsen Roser International S.A.R.L., Gaillac, France

[21] Appl. No.: 627,507

[22] Filed: Apr. 4, 1996

[51] Int. Cl.[6] ..... A01H 5/00

[52] U.S. Cl. ..... Plt./54.1

[58] Field of Search ..... Plt./54.1

[56] References Cited

PUBLICATIONS

GITTM UPOVROM listing for 'Evitwo' as per PBR 02300141 (GB) Oct. 28, 1993.

*Primary Examiner*—James R. Feyrer

[57] ABSTRACT

A White clematis characterized by: an outstanding flowering habit, producing many flowers on one stem; clear, white color; few green outer tepals; a longer flowering period than 'Duchess of Edinburgh'; and lasting longer as a cut flower than 'Duchess of Edinburgh.'

6 Drawing Sheets

BACKGROUND OF THE INVENTION

The present invention relates to a new and distinct variety of clematis plant known by the cultivar name 'Evitwo,' and formerly known under the breeder's reference name of Artic Queen. It was discovered as a chance seedling of unknown parentage in a cultivated area at St. Sampson's Parish, Guernsey, Channel Islands, Great Britain.

There are a number of varieties of white clematis of which the nearest to 'Evitwo' is believed to be the variety 'Duchess of Edinburgh.' The following unique combination of characteristics that are outstanding in 'Evitwo' have been repeatedly observed in asexually propagated progeny and distinguish it from 'Duchess of Edinburgh' and from all other varieties of which I am aware:

1. An outstanding flowering habit, producing many flowers on one stem;
2. A clear, white color;
3. Few green outer tepals;
4. A longer flowering period than 'Duchess of Edinburgh'; and
5. Lasting longer as a cut flower than 'Duchess of Edinburgh.'

This variety has not been observed under all possible environmental conditions. The phenotype of clematis plants can vary significantly with variations in environment such as temperature, light intensity, day length, and soil condition. The following observations, measurements and comparisons describe plants grown under growing conditions that are similar to those generally used in commercial practice.

Asexual reproduction of this new variety was by vegetative cuttings as performed at Guernsey, Channel Islands, Great Britain, and showed that the foregoing characteristics are established and transmitted through succeeding asexual propagations.

BRIEF DESCRIPTION OF THE PHOTOGRAPHS

The accompanying photographs show typical specimens of the foliage and flowers of this new variety, depicted in color as nearly true as it is reasonably possible to make the same in a color photograph of this character. The photographs were taken in June 1994 at a nursery located in St. Sampsons' Parish, Guernsey, Channel Islands, Great Britain.

Sheet 1 is a view of a cluster of flowers on a plant of 'Evitwo.'

Sheet 2 is a view of a single autumn flower of 'Evitwo' showing the tepal arrangement.

Sheet 3 is a view of flower buds of 'Evitwo.'

Sheet 4 is a rear view of a single flower of 'Evitwo.'

Sheet 5 is a view of leaves of 'Evitwo.'

Sheet 6 is a view of flowers on a plant of 'Duchess of Edinburgh' showing the greater quantity of green outer tepals of this variety.

The following is a detailed description of my new clematis cultivar grown under glass at a nursery in St. Sampsons' Parish, Guernsey, Channel Islands, Great Britain, throughout the flowering period. The color descriptions used herein employ terminology in accordance with The Royal Horticultural Society (London) Colour Chart, except where ordinary dictionary significance of color is indicated.

Classification:

*Botanical.*—Clematis cv. Evitwo.

*Commercial.*—Clematis.

Parentage:

*Seed parent.*—Unknown.

*Pollen parent.*—Unknown.

Plant:

*Form.*—Upright climbing or spreading.

*Growth.*—Medium growth. Height attained (First season): 2.5 m.

*Foliage.*—Deciduous, normally compact—tri-foliate, sometimes simple. Size: Medium. Quantity: Average. Color: New foliage: Upper side: Light Green (R.H.S. 137D). Underside: Light Green (R.H.S. 137C). Old foliage: Upper side: Green (R.H.S. 137A). Underside: Light green (R.H.S. 137C). Shape: Normally three ovate/cordate leaflets in pinnate form, sometimes simple. Texture: Upper Side: Glabrous. Underside: Ribbed and hairy. Edge: Normal. Serration: None. Petiole color: Top surface: Green. Underside: Green. Stipules: None. Internodes: Shape: Cylindrical. Length: About 12 cm to about 17 cm. Resistance to disease: Subject to any disease that normally affects clematis, but less prone to mildew than some clematis.

*Wood.*—New Shoots: Color: Light green. Bark: Smooth; light white hairs. Old Wood: Color: Light brown. Bark: Rough.

*Hardiness.*—Zone 4–9.

Flower:

*Blooming habit.*—Recurrent.

*Bud.*—Size: About 4 cm to about 5 cm length; about 2 cm to about 3 cm width. Form: Ovate. Color: Green/grey, hairy. Sepals: None (tepals only). Peduncle: Length: About 5 cm to about 10 cm. Aspect: Vertical. Strength: Erect. Color: Green (R.H.S. 143C). Bracts: None; outer tepals occasionally green.

*Bloom:*—Average size when fully open: About 10 cm to about 18 cm. Borne: Singly, but 5 to 7 flowers per flowering stem. Form: Double; outer tepals open to become flat; inner tepals remain ruffled. Number of tepals: Minimum of 12. Color: Outer tepals: Top surface: White (R.H.S. 155C). Undersurface: White (R.H.S. 155C with green mid rib. Inner tepals: Top surface: White (R.H.S. 155C). Undersurface: White (R.H.S. 155C). Base of tepals: White/green. General tonality from a Distance: White. Color change: As bloom ages, colors remain similar; may darken slightly to become creamy-white when very old. General Tonality at a distance: White.

*Tepals.*—Texture: Medium. Appearance: Inside: Satin. Outside: Matt. Form: Obovate. Arrangement: Regularly arranged in 'double' form. Petaloids in center: Occasionally. Persistence: Persistent. Fragrance: Slight. Lasting quality: Two weeks on plant, lasting longer than usual as a cut flower, typically 5 days.

Reproductive organs:

*Stamens, filaments and anthers.*—Arrangement: Regularly arranged. Color: Stamens: White base, yellow tip. Filaments: White. Anthers: Yellow.

*Pollen.13* Color: White to light cream.

*Styles.*—Bunched, even, average length.

*Stigmas.*—Color: White.

*Hips.*—None (but produces seed heads).

I claim:

1. A new and distinct variety of clematis plant named 'Evitwo' as herein shown and described.

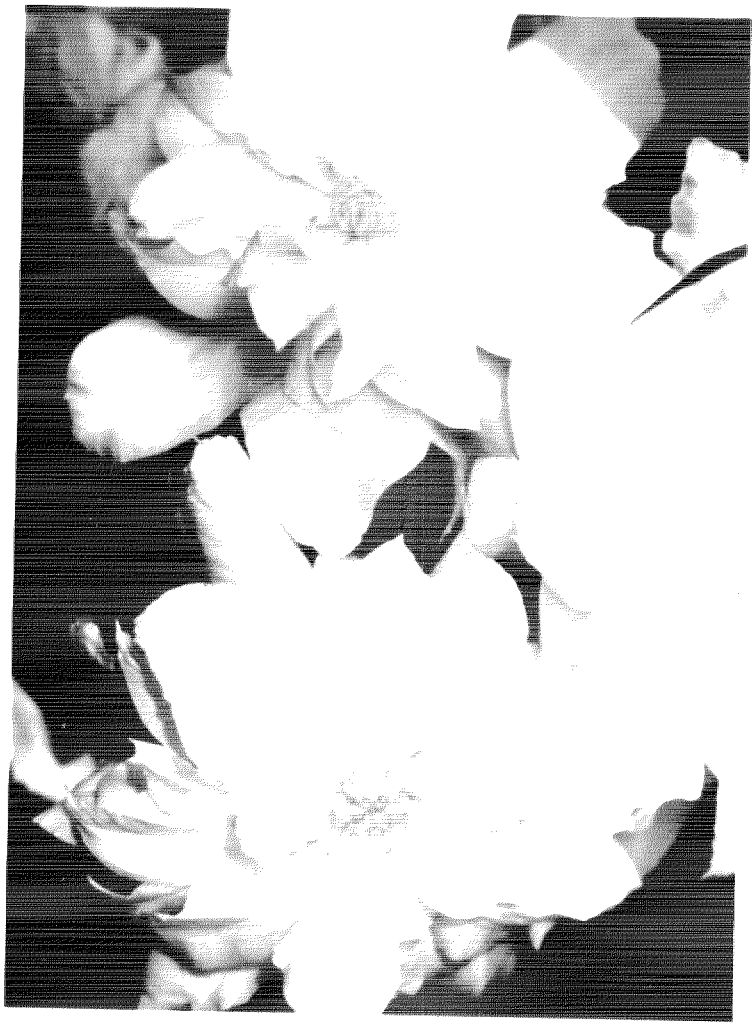

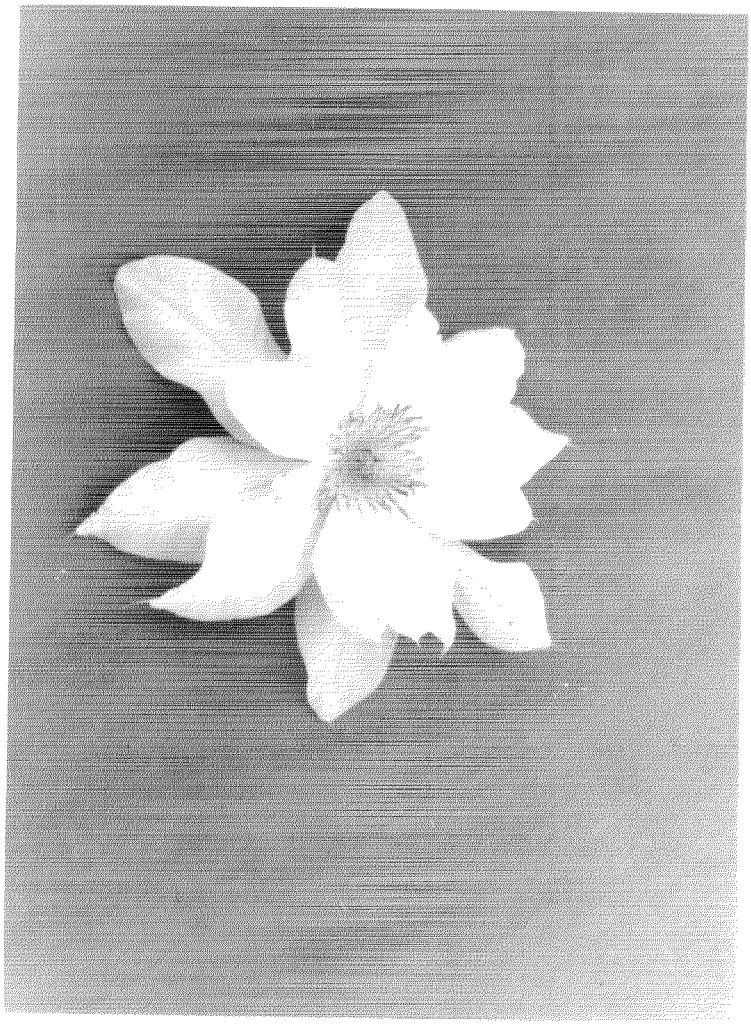

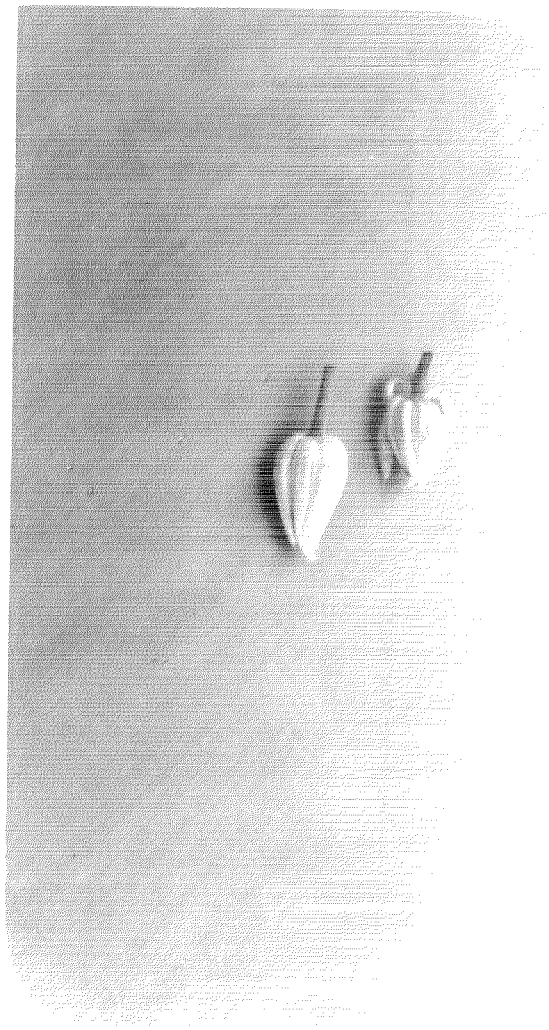

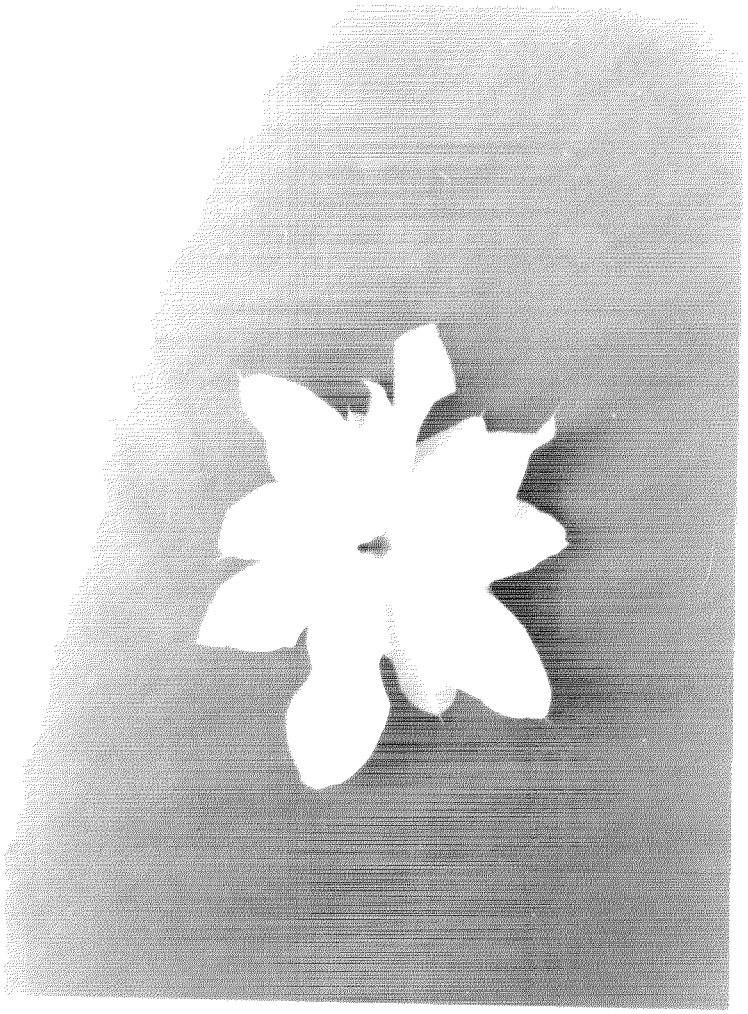

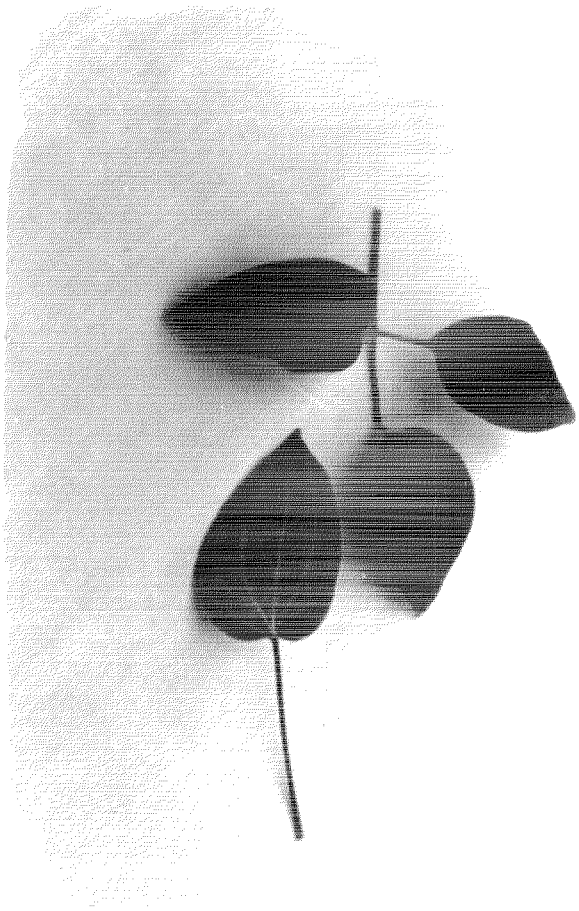

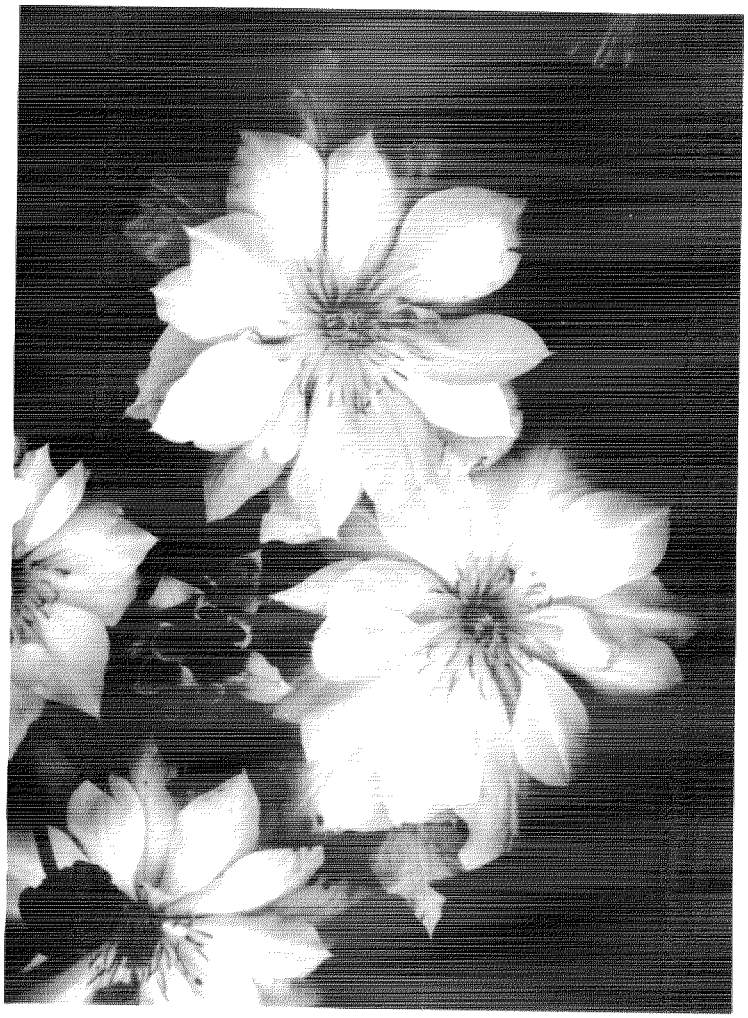

* * * * *